United States Patent [19]

Camps et al.

[11] Patent Number: 5,314,463
[45] Date of Patent: May 24, 1994

[54] BIPOLAR NERVE ELECTRODE

[75] Inventors: Antoine N. J. M. Camps, Eys, Netherlands; Pierre A. Grandjean, Bassenge, Belgium; Gary M. Johnson, Ramsey; Philip H. J. Lee, Woodbury, both of Minn.; Nicolaas M. H. Lokhoff, Kerkrade; Willem J. Van Driel, Heerlen, both of Netherlands

[73] Assignee: Medtronic, Inc., Minneapolis, Minn.

[21] Appl. No.: 47,211

[22] Filed: Apr. 14, 1993

Related U.S. Application Data

[62] Division of Ser. No. 795,942, Nov. 18, 1991, Pat. No. 5,241,957.

[51] Int. Cl.⁵ ............................................. A61N 1/04
[52] U.S. Cl. ................................................. 607/129
[58] Field of Search .......................... 128/784, 785, 786

[56] References Cited

U.S. PATENT DOCUMENTS

| | | | |
|---|---|---|---|
| 3,216,424 | 11/1965 | Chardack | 128/785 |
| 3,244,174 | 4/1966 | Wesbey et al. | 128/785 |
| 3,416,533 | 12/1968 | Fisher et al. | 128/786 |
| 3,474,791 | 10/1969 | Bentov | 128/786 |
| 4,026,300 | 5/1977 | DeLuca et al. | 128/785 |
| 4,541,440 | 9/1985 | Parsonnet | 128/785 |
| 4,590,946 | 5/1986 | Loeb | 128/784 |

*Primary Examiner*—William E. Kamm
*Attorney, Agent, or Firm*—Gregory P. Gadson; Harold R. Patton

[57] ABSTRACT

One aspect of this invention relates to a temporary heart wire, and external connector therefore, and the combination of the two, wherein the distal end of the heart wire includes a temporary affixation coil (8) and distal pacing (2) and sensing (1) electrodes connected by means of a coaxial helicoidally wound cable (3) to a proximal electrode (7) and a breakaway needle (6) which also serves as a proximal electrode. The lead is adapted to be inserted into a disposable connector having a snap aperture element (19) for receiving the breakaway needle, and about which the needle is broken, as well as electrical contacts (17, 18) for contacting the proximal electrodes and adapted to be connected to a temporary external pacemaker. According to another aspect of this invention, there is provided a permanent bipolar nerve electrode which includes two electrodes (52), (54) adapted to be positioned along the nerve trunk (58). The bipolar nerve electrode further includes an affixation coil (56) and a thin insulation layer or flap (57), this latter being adapted to be sutured to the surface of the patient's muscle to thereby preclude or limit stimulating electrical energy to be transmitted to adjacent muscles, this allowing for a more focused concentration of electrical energy to the nerve trunk (58) to be stimulated.

3 Claims, 12 Drawing Sheets

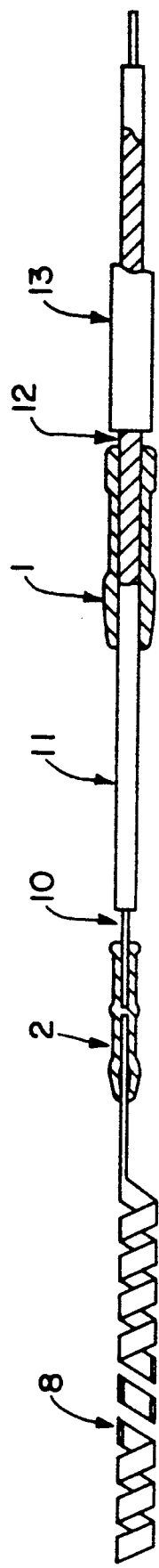
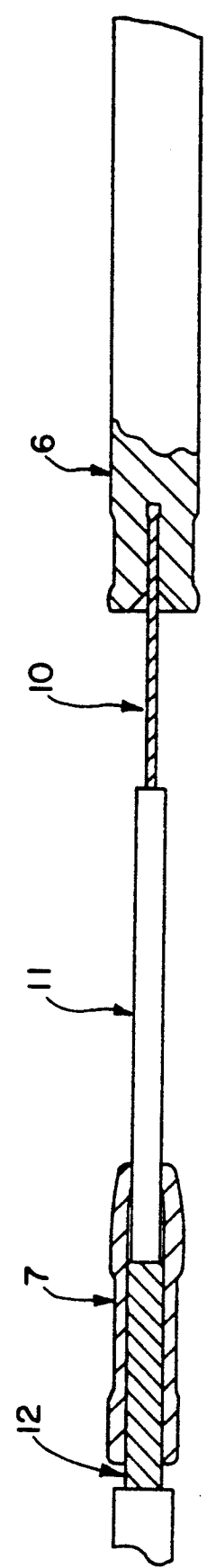
FIG. 6
FIG. 7

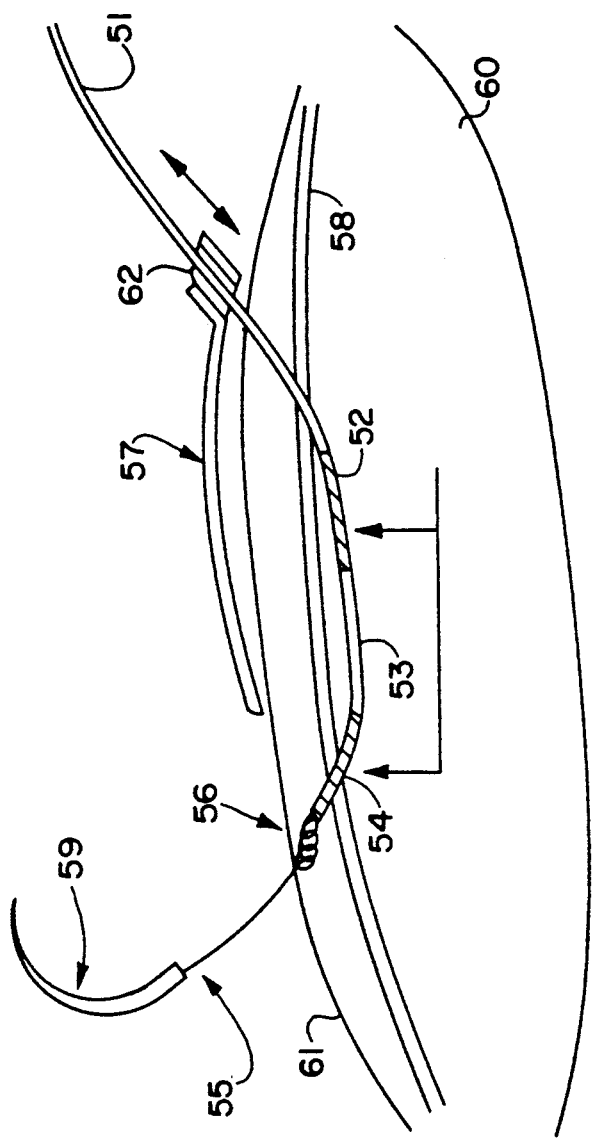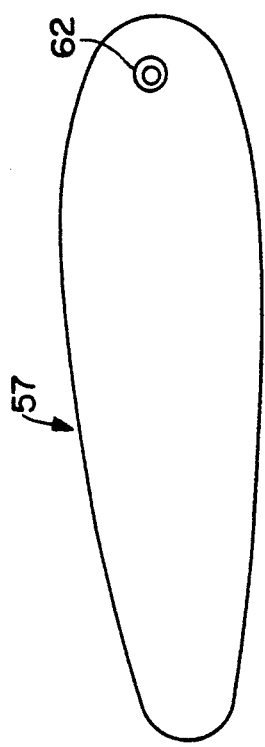

BIPOLAR NERVE ELECTRODE

This is a division of co-pending application Ser. No. 07/795,942, filed Nov. 18, 1991, now U.S. Pat. No. 5,241,957.

BACKGROUND OF THE INVENTION

1. Field of the Invention

The present invention relates to a bipolar temporary pacing lead which is temporarily used for post-operative myocardial stimulation, including pacing and sensing electrodes, and an affixation coil for lead anchoring as well as an external connector adapted for receiving the proximal end of the temporary lead. Another aspect of the present invention relates to a bipolar permanent nerve lead which is placed adjacent a nerve trunk to be stimulated including bipolar electrodes, an affixation coil, and an insulation flap for preventing unwanted transmission of electrical energy to surrounding muscle structure.

2. Description of the Prior Art

Temporary heart wires are known in the art, for example, U.S. Pat. Nos. 4,541,440 to Parsonnet and 4,341,226 to Peter Peters (assignee Medtronic), Temporary Lead with Insertion Tool.

Such devices are adapted to be placed in the heart wall by means of a curved needle wherein the electrodes remain within the heart wall and the proximal end of the lead is brought to the exterior of the patient's chest by means of a second straight needle, located at the proximal end of the heart wire.

Devices known in the prior art have drawbacks as their construction is somewhat primitive in that the electrodes constitute merely exposed portions of the conductive wire within the lead, no means is provided for affixing the bipolar electrodes within the heart and dislodgement is a problem, and the lead itself tends to be stiff as it is constructed of two separate wires which lie in a side-by-side configuration causing stiffness in at least one direction of bending.

Also, there remains the problem of providing an external connector for the proximal end of the wire which extends externally from the patient's chest. There is a need for a convenient, easy-to-use, interface, or connector, between the lead per se and the external temporary pulse generator. Such a connector must not require substantial electrical or mechanical manipulations on the part of the surgeon, should be comfortable to the patient, and the electrical contacts must be secure and reliable. Further, the connector should be reasonably economical to manufacture, and, preferably, even disposable.

In regard to nerve wires, these wires in the past were unipolar, were more particularly adapted for implantation near nerve branches, and did not have affixation means. Further, in the prior art, no means was provided for shielding adjacent muscle structure from unwanted stimulation.

SUMMARY OF THE INVENTION

This invention relates to a temporary bipolar pacing lead having a proximal and a distal end wherein there are included discreet, dedicated, pacing and sensing electrode elements at the distal end as well as a coil affixation member which is integral with a plastic monofilament element connected to the curved needle.

The lead includes a coaxial wire having helicoidally wound discreet stainless steel strands providing great flexibility and excellent mechanical and electrical connecting properties.

The proximal end of the electrode includes a breakaway needle which constitutes one of the proximal electrodes with the proximal end of the lead being adapted for entry into a disposable plastic connector.

The surgeon has merely to thread the breakaway needle into the entrance aperture of the disposable plastic connector and exit the needle portion through the exit aperture. Because of the construction of the breakaway needle and the disposable plastic connector, the needle will click firmly into place within the connector housing at a fulcrum element. By closing the cover of the disposable plastic connector, a secure fixation will be made between the breakaway needle (which functions as one proximal electrode), and the other proximal electrode, with the electrical contact elements within the disposable plastic connector which are, in turn, connected to the external pacemaker. The remaining part of the needle can be removed by bending the needle, causing it to break. The broken proximal lead end will remain within the housing. In this way, a secure mechanical and electrical contact is established.

The disposable connector is preferably made of injection molded plastic, which is relatively inexpensive to manufacture, and includes an insert member on which the fulcrum and other support elements can be integrally molded.

Numerous advantages accrue to this construction and will be made apparent upon reading the more detailed description of the preferred embodiment and the claims.

BRIEF DESCRIPTION OF THE DRAWINGS

FIG. 6 shows the details of the distal end of the lead.

FIG. 7 shows details of the proximal end of the lead.

FIG. 18 shows a side view of the permanent bipolar nerve electrode implanted.

FIG. 19 shows a top view of the insulating flap of the permanent bipolar nerve electrode.

DETAILED DESCRIPTION OF THE DRAWINGS

Figure 1:
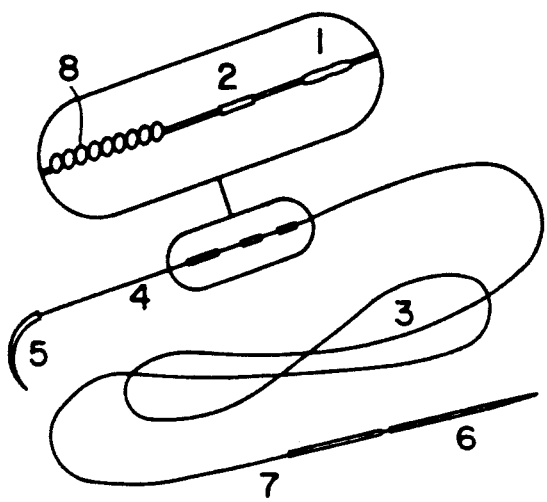
FIG. 1 shows the heart lead constructed according to the teachings of this invention.

FIG. 1 shows the bipolar temporary myocardial pacing lead constructed in accordance with the teachings of this invention.

The lead includes a curved needle (5) adapted to be used to penetrate the myocardium preparatory to drawing the heartwire and its electrodes within the myocardium.

The curved needle (5) is connected to monofilament strand (4) including affixation coil (8), the coil and the strand comprising one length of polypropylene, the coil insuring a good temporary fixation of the wire in the heart and prevents dislodgements which might occur with a smooth tipped lead.

Fixation coil (8) is connected to pacing distal electrode (2) which, in turn, is mechanically, but not electrically, connected to sensing distal electrode (1). Coil (8) and electrodes (1) and (2) are best seen in the enlarged breakout section seen in FIG. 1, and also in FIG. 6.

The electrodes (1) and (2) are preferably made of stainless steel which is suitable for temporary applications.

Sensing distal electrode (1) is mechanically connected by coaxial lead wire (3) to the proximal ring electrode (7) which, in turn, is mechanically connected to breakaway needle (6).

Figure 2:
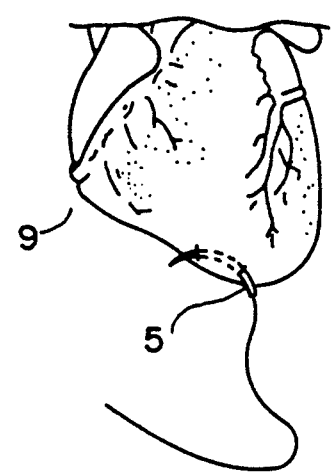
FIG. 2 shows the lead being inserted into the myocardium of the heart.

FIG. 2 shows the curved needle (5) penetrating the heart (9) preparatory to drawing the bipolar lead into the myocardium.

Figure 3:
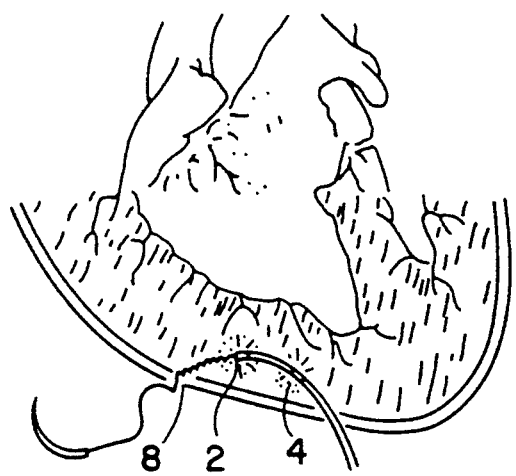
FIG. 3 shows the lead positioned within the myocardium of the heart with both distal electrodes being within the myocardium.

FIG. 3 shows the lead position within the myocardium with affixation coil (8), pacing electrode (2) and sensing electrode (1), being located within the myocardium of the ventricle.

Figure 4:
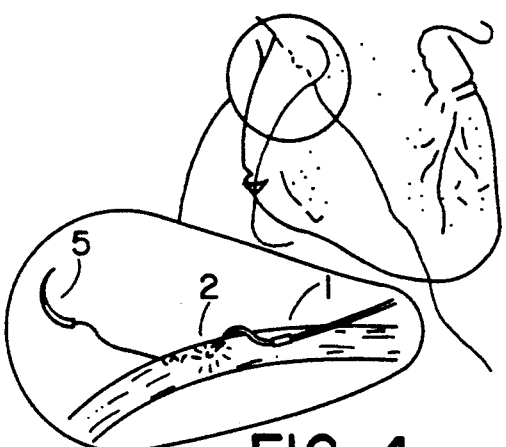
FIG. 4 shows the lead positioned within the atrium by two passes of the curved needle resulting in the insulation being visible between the electrodes.

For implantations in the atrium, the technique shown in FIG. 4 is preferred. Pursuant to the procedure of FIG. 4, the surgeon would make two passes with curved needle (5) with a portion of the lead between the pacing, or tip, electrode (2) and sensing, or ring, electrode (1) being positioned above the surface of the myocardium as shown. This particular technique is used since the wall of the atrium is much thinner than that of the ventricle and this technique safeguards against accidental penetration of the myocardium.

Figure 5:
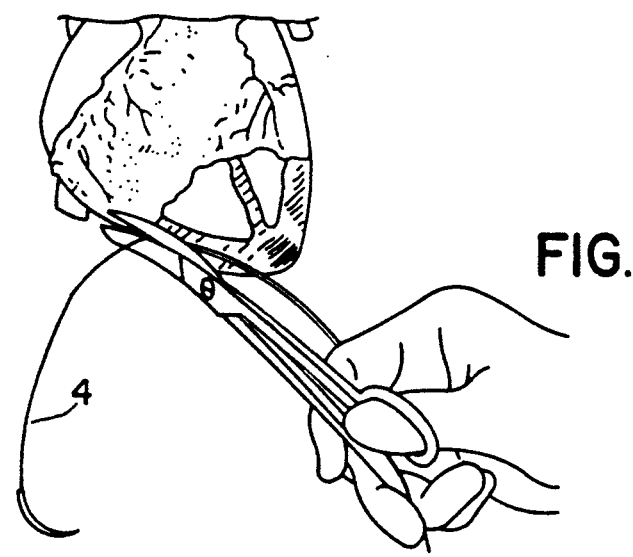
FIG. 5 shows the removal of the curved needle from the temporary implanted lead so that the remaining part will resume its coil shape in the myocardium.

FIG. 5 shows the step in the implantation procedure whereby the surgeon cuts plastic wire (4) at the surface of the heart wall, leaving affixation coil (8) embedded in the heart wall.

FIG. 6 shows the affixation coil and distal electrodes in a greater detail. There is seen affixation coil (8) including eight right handed wound turns.

The coil is crimp affixed to tip, or pacing, electrode (2) which is itself crimp connected to inner conductor filaments (10). The inner conductor filaments (10) are surrounded by inner insulation layer (11) which is mechanically connected to ring or sensing electrode (1).

Sensing electrode (1) is crimp affixed to the outer conductor filaments (12) which are enrobed within outer insulator layer (13).

FIG. 7 shows the proximal electrodes in greater detail. Proximal ring electrode (7) is crimp connected to the outer conductor filaments (12), being thereby in electrical contact with distal sensing electrode (1)

Ring electrode (7), on its proximal side, is crimp connected to the outer conductor filaments (12).

Inner conductor filaments (10) are crimp connected to the end of breakaway needle (6), the needle thereby constituting one of the proximal electrodes and being in electrical contact with distal pacing or tip electrode (2).

Figure 8:
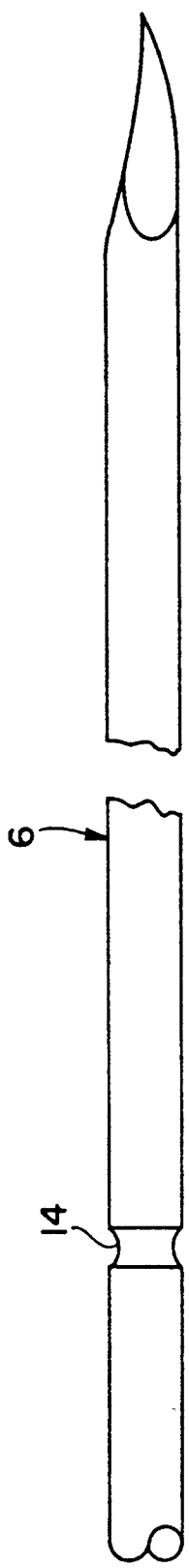
FIG. 8 shows the breakaway needle.

FIG. 8 shows breakaway needle (6) in greater detail. As is seen in the Figure, breakaway needle (6) includes an indentation (14) which weakens the needle at that point allowing the surgeon to snap the needle off at this point, as will be discussed.

Figure 9:
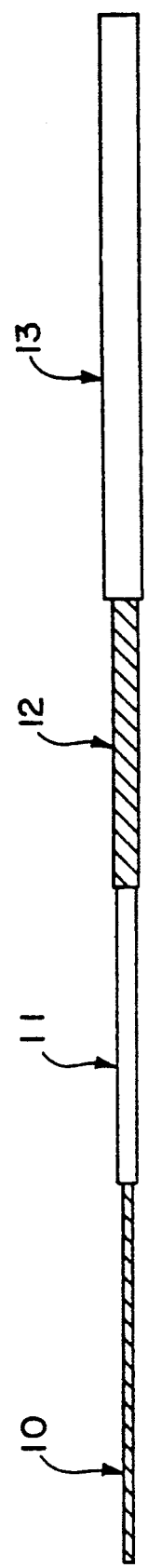
FIG. 9 shows the detail of the coaxial cable.

FIG. 9 shows the coaxial insulated wire (3) in greater detail. Inner conductor filaments (10) include 37 separate stainless steel strands each, in the preferred embodiment, each filament or wire having a diameter of 0.026 mm. Inner insulation layer (11) is made of Teflon ® and covers and insulates inner conductor filaments (10). Outer conductor filaments (12) include 24 stainless steel strands wound in a helicoidal manner over inner insulator layer (11), each strand having a diameter of 0.044 mm. The helicoidal winding is significant as it provides for an especially flexible construction. The outer insulator layer (13) covers the outer conductor filaments. According to a preferred embodiment, insulator (13) comprises a polyethylene coating, with the insulator being preferably color coded.

After the surgeon has positioned the lead within the myocardium, and snipped off curved needle (5), the surgeon would utilize breakaway needle (6) to pierce the thorax of the patient to bring the proximal end of the lead to the exterior of the patient's chest.

Once the proximal end of the lead is brought to the exterior of the patient's chest, it should be affixed in a suitable manner allowing for convenient, safe, connection to the external pulse generator, as well as being comfortable to the patient.

Figure 10:
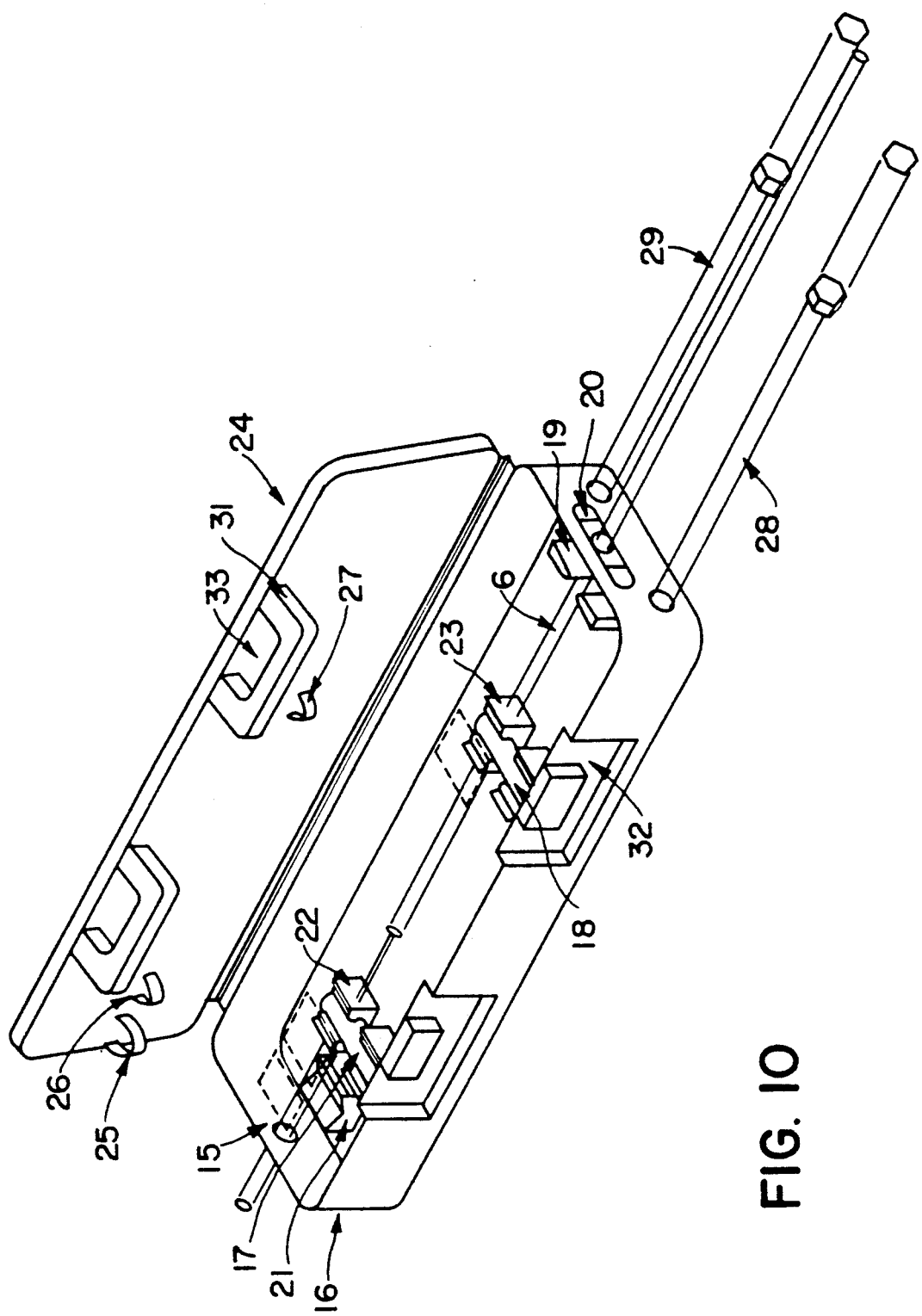
FIG. 10 is a perspective view of the disposable plastic connector.

FIG. 10 shows a disposable connector constructed in accordance with the teachings of this invention which is adapted functionally to interact with the aforedescribed lead to produce a particularly advantageous lead-connector combination.

The connector of FIG. 10 would be positioned outside of the patient's chest and, after breakaway needle (6) has been drawn through the patient's chest to the exterior, the needle is inserted into entry aperture (15) and drawn through the connector housing (16) passing over metallic electrical contacts (17) and (18), passing through flexible snap aperture (19), and finally being drawn through exit aperture (20), with the sharp end of the needle protruding from exit aperture (19) to the exterior of the connector.

The indentation in the breakaway needle discussed in connection with FIG. 8, would be drawn into snap aperture (19) and would click firmly into place, being held by the spring action of the flexible snap aperture.

The disposable connector includes cover (24) adapted to be snapped down and hold firmly in place the lead, the ring electrode, and the needle. This locking feature is effected by three holding loops (25), (26), and (27), which, as seen, are generally horseshoe shaped, and which are constructed of a flexible material and have a spring action.

When the cover is closed, lead holding loop (25) would press against and, by its flexible spring construction, hold the lead against lead support block (21) so that movements of the patient will not disengage the lead. Similarly, ring holding loop (26) would press against and hold firmly the proximal ring electrode (7) against ring contact (17), and needle holding loop (27) would press and hold firmly the shaft of the needle (6) against needle contact (18).

Two cables (28) and (29) are positioned within the connector box and would be connected, respectively, to needle contact (18) and ring contact (17), these cable connections not being shown in the drawing for simplicity.

After the proximal end of lead (3) has been brought into the disposable connector and properly positioned, cover (24) is snap locked into the connector housing (16). This snap locking is effected by cover spring action closing loops (30) and (31) which would fit snugly into the indentations in the wall of the housing, generally indicated at (32).

With the indentation being held by the snap aperture (19), and the cover being closed, the surgeon would simply bend the end of the breakaway needle (6) in a horizontal direction, which would cause the needle to break at the snap aperture (19). As the snap aperture is located within the connector, there would be no sharp edge protruding to the exterior, a valuable safety feature. It will be noted that the exit aperture (20) is in the form of a horizontal slot which allows for the bending of the needle about the fulcrum of the snap aperture.

The disposable connector and the proximal end of the lead are dimensioned to cooperate so that when the notch in the breakaway needle is positioned in snap aperture (19), the distal length of the needle will lie along, and be in electrical contact with needle contact element (18). Further, proximal ring electrode (7) will automatically lie along and be in electrical contact with ring contact element (17).

Ring contact element (17) is supported by ring support block (22) and needle contact element (18) is supported by needle support block (23). Further, there is provided lead support block (21) which is positioned under the insulated portion of the coaxial lead and which serves to hold the lead firmly within the connector, as will be further explained hereinafter.

Figure 11:
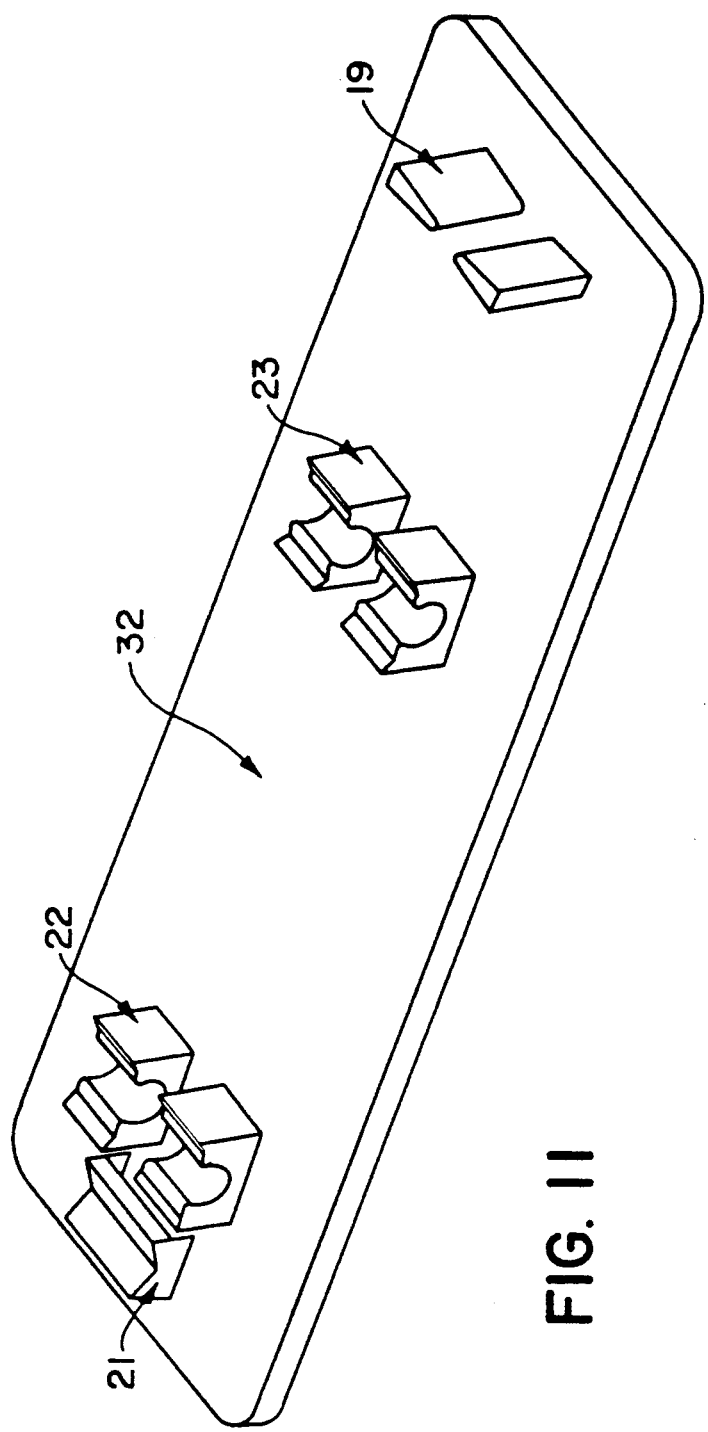
FIG. 11 shows the integrally molded insert for the connector.

According to a preferred embodiment, the disposable connector is made of two injection molded parts, one of these parts, the insert element being depicted in FIG. 11.

Figure 12:
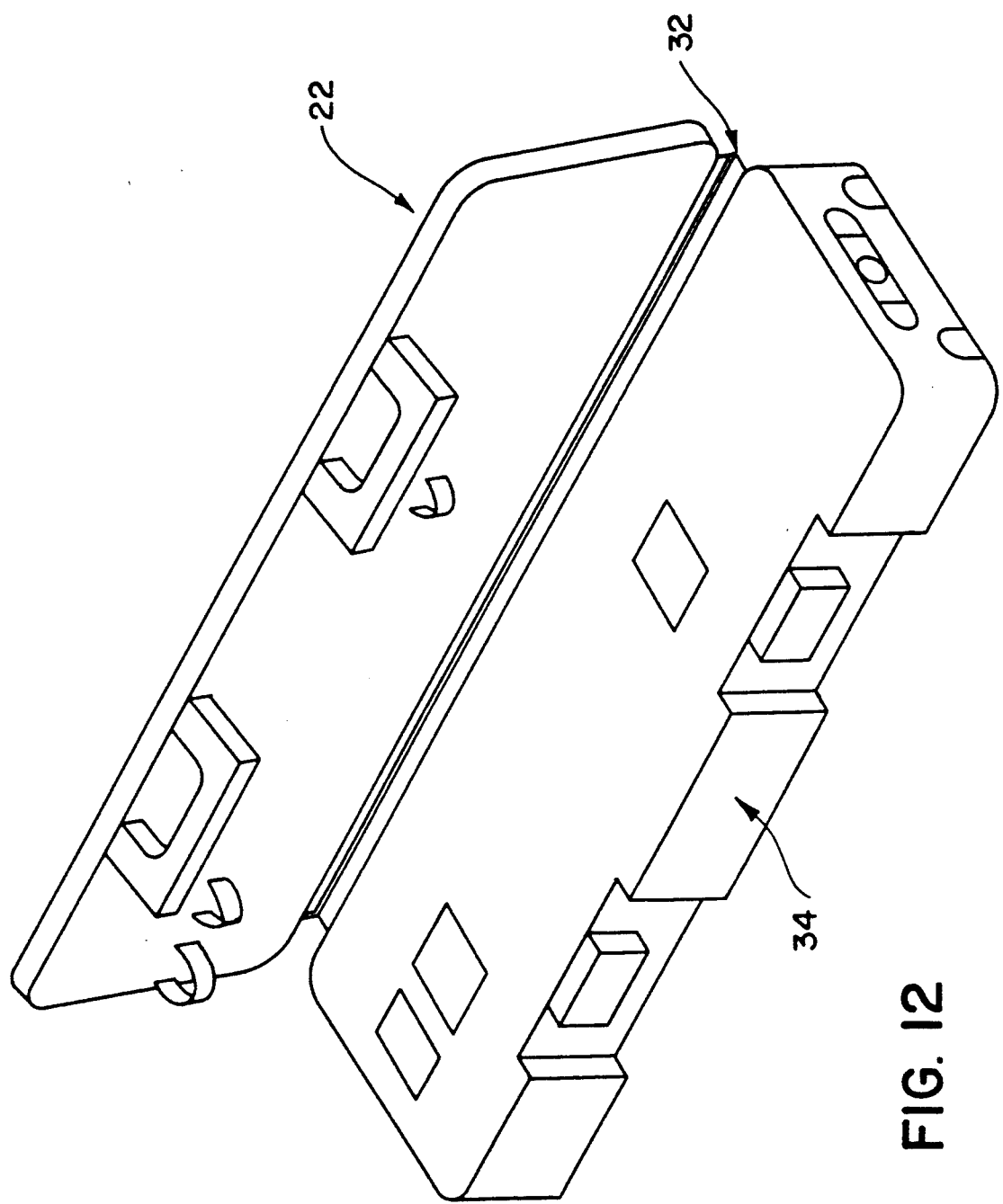
FIG. 12 shows the integrally molded housing for the connector with cover.

This insert element would be fitted into the housing seen in FIG. 12. The snap aperture elements (19) as well as the support blocks (21), (22), and (23), seen more clearly in FIG. 11, are integrally molded with the base (32) of the insert in the sense that all of these elements constitute a single injection molded component. This insert element would then be simply inserted into housing member seen in FIG. 12, with the cover (24) ultimately being connected by a hinge (32) to connector housing (16).

Figure 13:
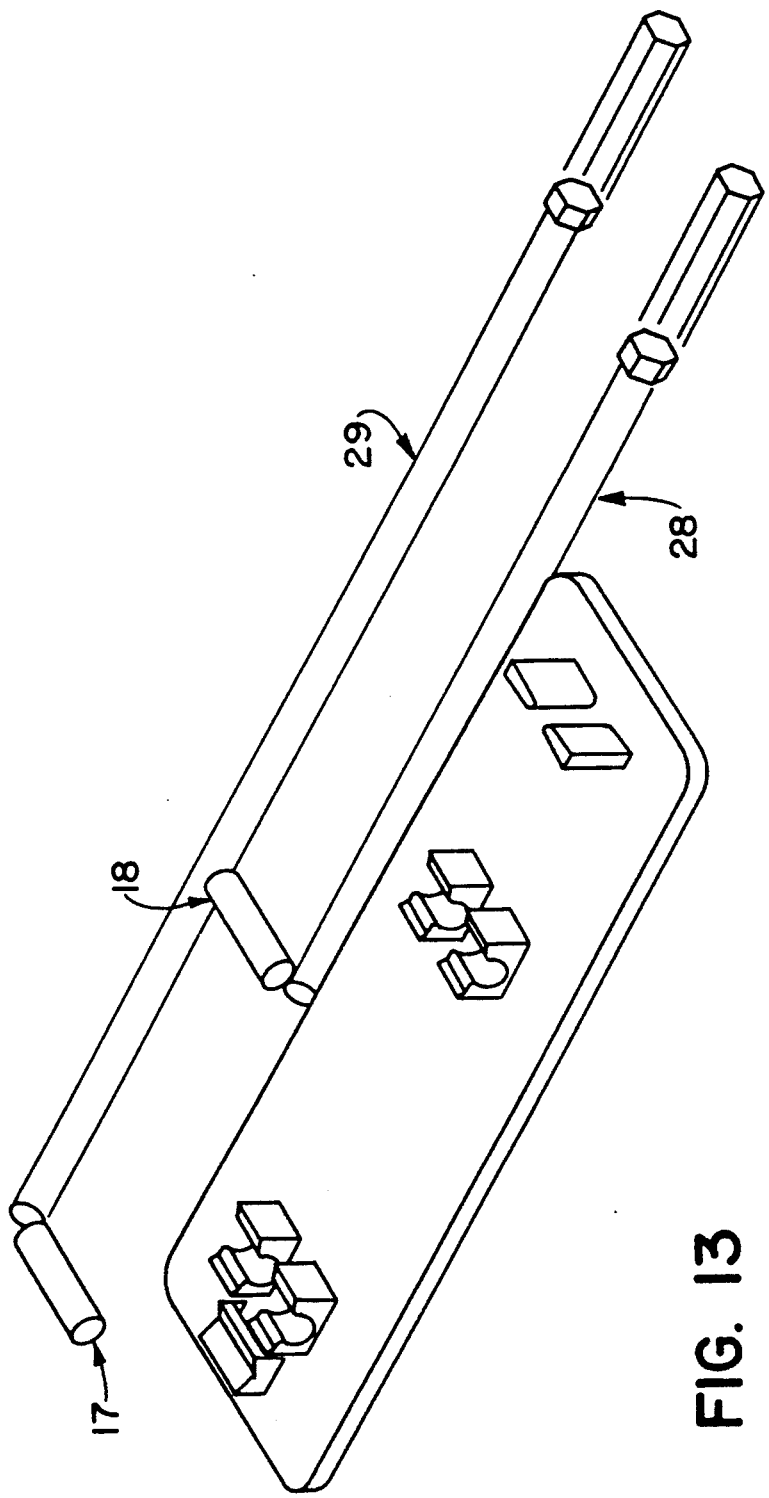
FIG. 13 shows the insert and cable connections thereto.

FIG. 13 shows in greater detail the relative positioning of external pacemaker cables (28) and (29) and the electrical contacts (17) and (18).

Figure 14:
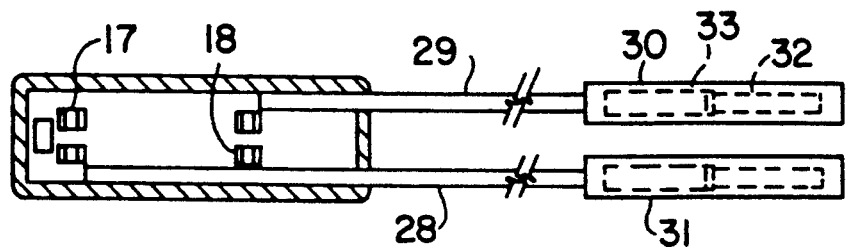
FIG. 14 shows a top view of the connector with protective sleeves at the distal end of the leads.

FIG. 14 depicts a further aspect of this invention which resides in the provision of protective sleeves at the pin connectors which are adapted to be connected to an external pacemaker.

FIG. 14 shows cables (28) and (29) which are adapted to be connected to an external pulse generator and which are encased in Teflon ® insulation. As discussed previously, cables (28) and (29) are connected to electrical contacts (17) and (18) located in the disposable connector, which is in turn in communication with the patient's heart via the temporary bipolar heart wire.

At the distal end of the pulse generator cables (28), (29), are pin connectors (32) and tubing shanks (33) which are adapted to be connected to the pulse generator.

Protective sleeves (30) and (31) surround and electrically shield the pin connectors (32) and tubing shanks (33).

The protective sleeves (30) and (31) are made of silicon rubber.

The protective sleeves (30) and (31) are adapted to slide over the outer surface of the cables (28) and (29), thereby to expose or protect the pin connectors (32).

These protective sleeves are significant in that, when the cables (28) and (29) are not connected to a pulse generator, it is important that the cable ends be protected from any accidental electronic discharge as the cables are, as mentioned, connected directly to the patient's heart via the heart wire.

The protective sleeves (30) and (31) thus insure that the external pacemaker cables are not subject to unwanted electrical discharge or do not accidently come into electrical contact with each other.

Figure 15:
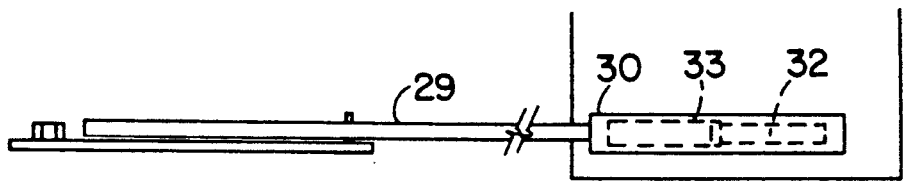
FIG. 15 shows a side view of the protective sleeves.

FIG. 15 shows a side view of the external pacemaker cable (29), protective sleeve (30), pin connector (32), and tubing shank (33).

Figure 16:
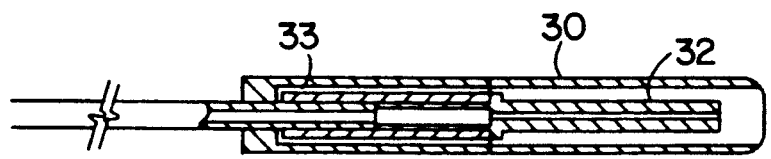
FIG. 16 shows an enlarged cross sectional view of the protective sleeve positioned at the distal end of the lead.

FIG. 16 shows a more detailed view of the slidable protective sleeve (30), positioned around the pin connector (32) and the tubing shank (33).

As mentioned, this lead is intended for temporary use only, typically approximately two weeks. When it is time to remove the lead, the surgeon would simply pull on the lead, very carefully, and withdraw the lead from the patient's heart and chest. The affixation coil is be flexible enough to allow the heart wire to be gently pulled from the myocardium without damaging the myocardium.

According to another aspect of the invention there is disclosed a bipolar electrode which is particularly adapted for nerve stimulation.

Figure 17:
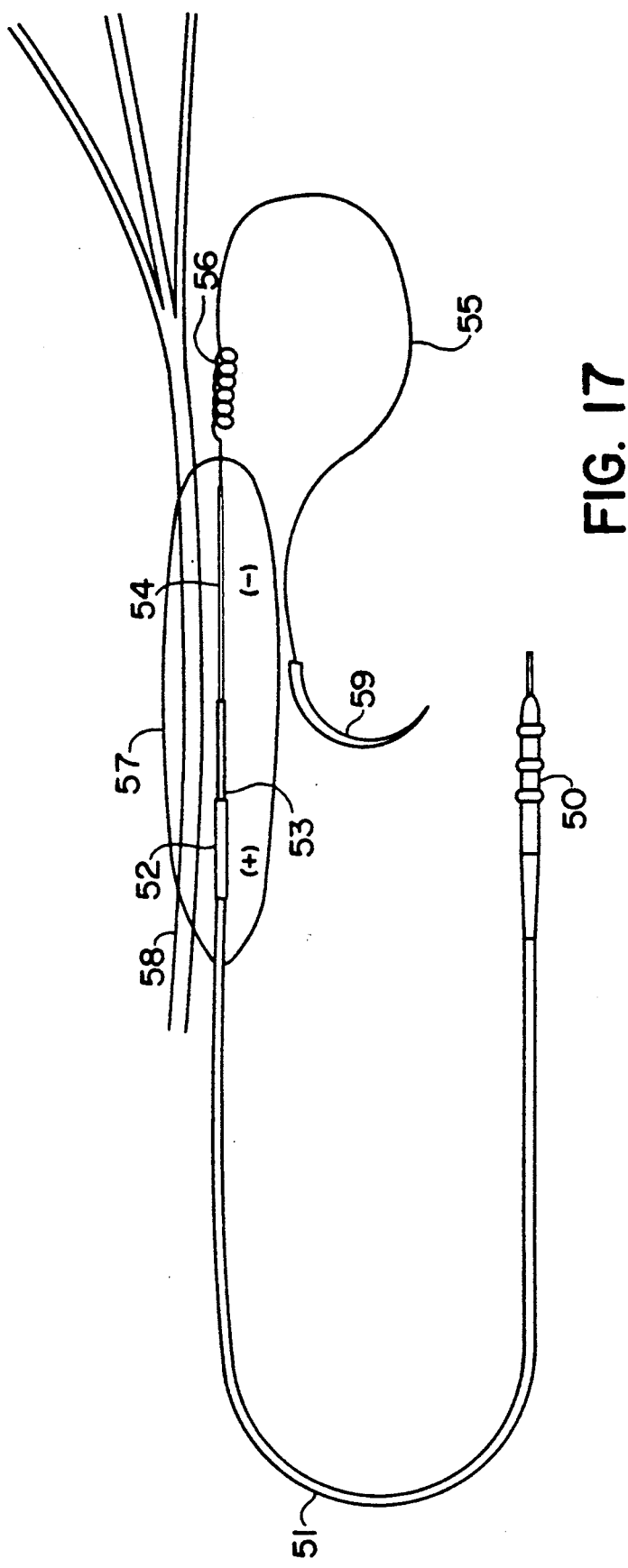
FIG. 17 shows the permanent bipolar nerve electrode.

FIG. 17 shows a bipolar nerve electrode which includes a bipolar connector (50) adapted to be connected to a pulse generator.

The bipolar connector (50) is connected via coaxial cable (51) to the stimulating electrodes (52) and (54).

The outermost conductor of coaxial cable (51) is electrically connected to a first, or indifferent, electrode (52). The other, or innermost conducting wire of coaxial cable (51) itself constitutes the second electrode, the stimulating electrode (54); that is to say, stimulating electrode (54) is the exposed end portion of the internal conductor of coaxial cable (51).

The current which flows between electrodes (52) and (54) stimulates the nerve.

Positioned between the outermost conductor of coaxial cable (51) and innermost conducting wire of coaxial cable (51) is insulating sheath (53) which is made of any appropriate coaxial insulator.

As seen in FIG. 17, stimulating electrode (54) is mechanically connected to a polypropylene wire (55).

Polypropylene wire (55) includes affixation coil (56) which is adapted to help hold the lead in place once it has been positioned within the muscle as will be discussed hereinafter. Polypropylene wire (55) is in turn mechanically connected to insertion needle (59).

Positioned on the outer surface of coaxial cable (51) is an insulation layer or flap (57) which comprises a relatively thin, flat, flap or layer of silicone insulation which is preferably reinforced with dacron, such as a dacron mesh enveloped within the insulative flap (57). As will be discussed, although not seen in FIG. 17, there is actually a small aperture or hole in flap (57) through which passes lead (51) which allows the flap appropriately to be positioned along the length of the lead. The flap, as seen from above in FIG. 17, is somewhat oval or "leaf-like" in shape. As will be discussed, as the flap is slideably connected to lead (51) only at its left hand end, the right hand end of flap (57) is free to be lifted up, away from the lead (51) and electrodes (52) and (54).

Current density can be changed by varying the length of the electrode (54) which increases or decreases the amount of exposed surface area of the electrode (54) which electrode is, as discussed above, the inner conductor of coaxial cable (51). This can be effected by sliding electrode (54) within insulating sheath (53). Similarly, the distance between electrodes (52) and (54) could be made adjustable by sliding insulating sheath (53) within electrode (52) and within the outer conductor of coaxial cable (51). Slideability is not required as it may be that the desired exposure and distances are known at the time of manufacture and, in such case, slideability is not needed.

According to this invention, this nerve electrode is particularly adapted to stimulate the main nerve trunk, and not the branches, of the thoraco-dorsal nerve. For such an application, the length of the stimulating electrode (54) would be approximately 0.5 cm to 1.5 cm, the length of the exposed insulating sheath (53) would be approximately 1.0 cm, and the length of the indifferent electrode (52) would be approximately 0.5 cm. The flap would be about 3.5 cm in length and 2.0 cm wide.

In operation, the muscle is exposed by the surgeon and the bipolar nerve electrode is inserted into the exposed muscle surface by means of insertion needle (59) and positioned with the stimulating electrode (54) and indifferent electrode (52) being placed in proximity to, and in parallel with, nerve trunk (58).

The thin insulation layer (57) will be slid along the lead (51) and brought to the surface of the exposed muscle into which the electrodes have been inserted. As will be discussed in connection with FIG. 18, flap or layer (57) is laid flat along the outer surface of the exposed muscle and is sutured about its periphery to the muscle surface.

By this means, when the nerve is electrically stimulated, the insulation layer (57) will function to block the electrical stimulation pulses from interfering extensively throughout the neighboring muscle structure of the patient. By virtue of this feature, therefore, the electrical energy may be applied in a more focused manner to the nerve trunk and unwanted muscle stimulation is avoided or made minimal.

FIG. 18 shows a side view of the bipolar nerve electrode implanted into muscle (60) adjacent nerve trunk (58). There are seen electrodes (52) and (54) placed in proximity to, and roughly parallel with, main nerve trunk (58). The nerve wire is permanently held in place within muscle mass (60) by means of affixation coil (56) which remains embedded in muscle mass (60) and also by the flap which is sutured to the muscle and affixed to the cable also by suturing. The fact that the flap includes dacron reinforcement allows for good tear resistance and thus permanence.

Insertion needle (59) and polypropylene wire (55) are adapted to be snipped off at the surface (61) of muscle (60) after implantation.

Insulation layer or flap (57) is seen in a side view positioned flat along the exposed surface (61) of the muscle. As seen in FIG. 18, the flap (57) has an aperture (62) which allows the flap (57) to slide along the surface of the coaxial cable (51).

When the electrodes are properly placed adjacent nerve trunk (58) and the flap (57) is properly positioned on the muscle surface (61), the outer edges of the flap (57) are sutured to the surface of muscle (61) and the flap, at aperture (62), may be glued to the coaxial lead (51) by the physician, if desired, such as by silicone glue. In this manner, the flap will rest in place on the surface (61) of the muscle (60) permanently. Further anchoring of the lead, if desired, can be accomplished by the physician suturing or otherwise securing an anchoring pledget, such as a silicone disc, to the surface of the muscle after passing the polypropylene wire through the disc.

FIG. 19 shows a top view of the flap (57) showing the insertion aperture (62).

Figure 20:
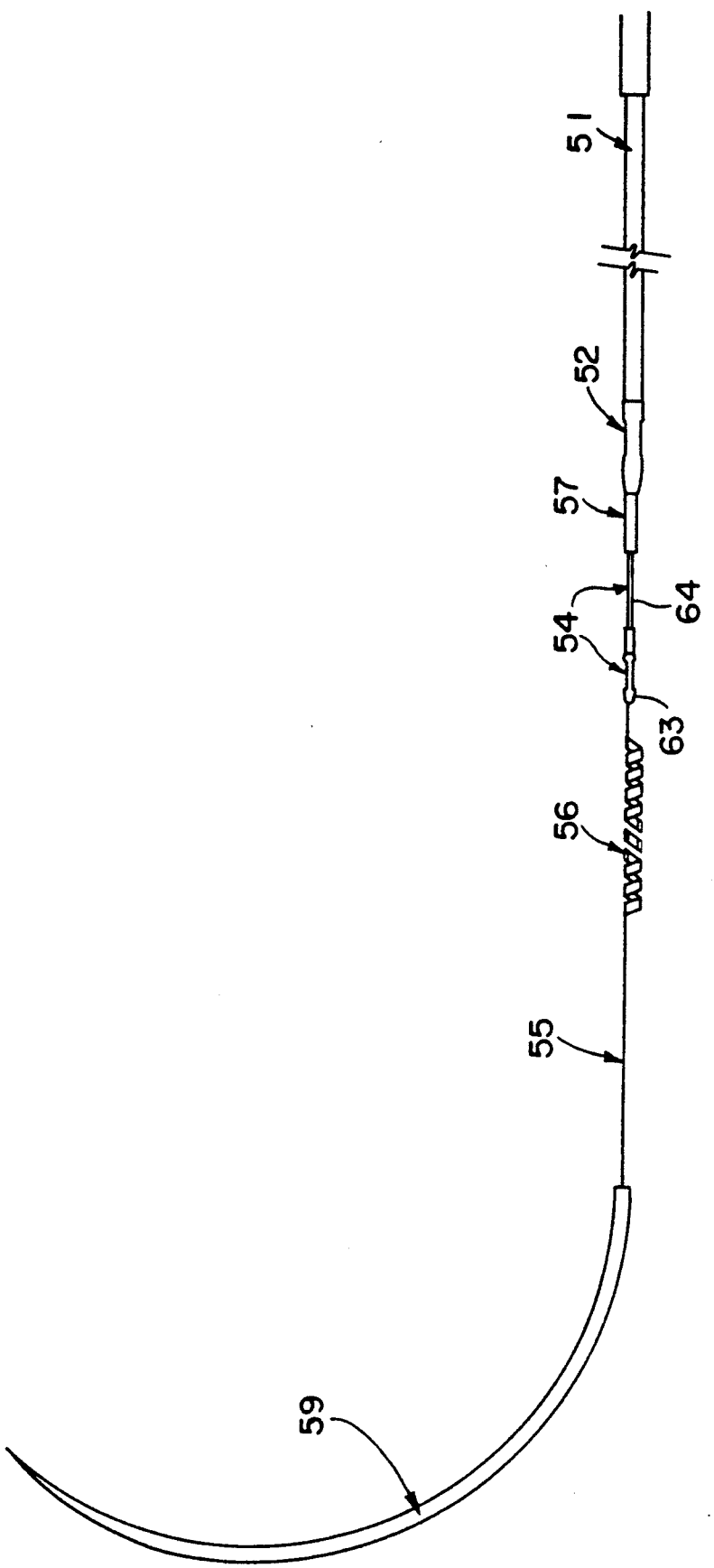
FIG. 20 shows a more detailed view of the permanent bipolar nerve electrode.

FIG. 20 shows the bipolar nerve electrode in more constructional detail. There is seen insertion needle (59) connected to polypropylene wire (55) which is integral with affixation coil (56). The polypropylene wire is connected to the stimulating electrode (54) which includes a tip (63) connected to the coil (64) which constitutes the inner conductor of the coaxial cable (51).

Positioned around coil (64) is an insulating layer (57) and positioned around insulator (57) is electrode (52) which is in the form of an electrode ring.

Figure 21:
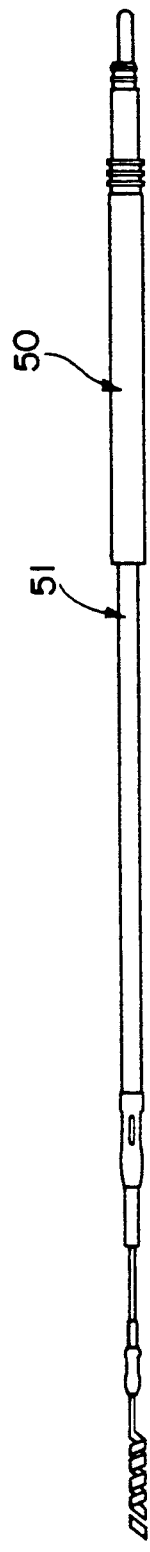
FIG. 21 shows a more detailed view of the connector of the permanent bipolar nerve electrode.

FIG. 21 shows in more detail the bipolar connector (50) connected to cable (51). This bipolar connector is adapted to be connected to a pulse generator.

Figure 22:
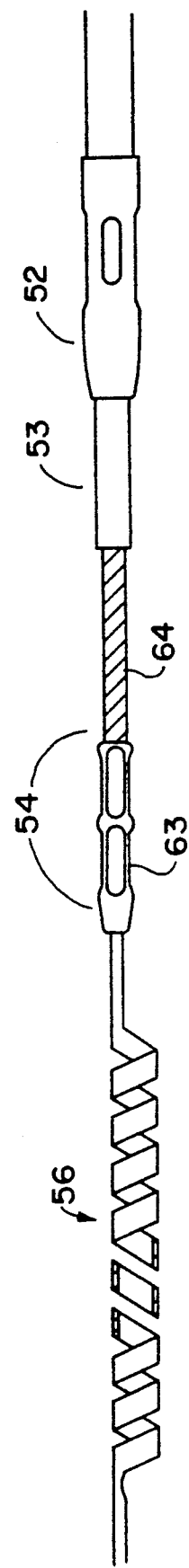
FIG. 22 shows an even more detailed view of the permanent bipolar nerve electrode.

FIG. 22 shows in still greater detail the construction of the electrode portion of the nerve electrode. There is seen affixation coil (56) connected to stimulating electrode (54) which comprises tip (63) and inner coil (64). The indifferent electrode is seen at (52) with insulating sheath at (53).

As mentioned, it would be possible to provide for adjustability of the length of electrode (54) by constructing sheath (53) to be slidable along coil (64). Alternatively, some adjustability can be obtained by simply paring away portions of sheath (53) prior to implantation so as to provide for greater exposure of coil (64).

Further adjustability could be obtained, if desired, by providing that electrode (52) be slidable over the surface of sheath (53). This would allow the distance between the two electrodes (52) and (54) to be adjusted.

While the invention has been described above in connection with the particular embodiments and examples, one skilled in the art will appreciate that the invention is not necessarily so limited and that numerous other embodiments, examples, uses and modifications of and departures from the embodiments, examples and uses disclosed may be made without departing from the inventive concepts.

We claim:

1. A bipolar nerve electrode for permanent implantation into a muscle (60) and adjacent a nerve (58) for simulation of the nerve, said nerve electrode comprising:
- a first (52) electrode means;
- a cable means (52) coupled to said first electrode, and including a conductor (54) having an exposed distal end which exposed end comprises a second electrode means (54), said first (52) and second (54) electrode means providing opposite polarity electrical energy to the nerve (58);
- an insulating means (53) coupled between said conductor (54) and said first electrode (52); and
- an insulating flap means (57) coupled to said cable means (51) comprising means for coupling said flap means to a surface (61) of the said muscle (60) for shielding adjacent muscle structure from the electrical stimulation provided by said first (52), and second (54) electrodes thereby concentrating the stimulation current field to the nerve,
- wherein said flap means (57) comprises suture means for suturing said flap means to said surface (61) of said muscle (60), and said flap means also comprises an aperture means (62) coupled to said cable (51) for facilitating sliding of the flap along the cable (51).

2. The nerve electrode of claim 1, including, in combination, a guide wire (55), an affixation means (56), and an insertion needle (59), wherein the affixation means (56) is integral with said guide wire (55) and comprises embedding means for permanently embedding said nerve electrode in said muscle (600 and said guide wire (55) is adapted to be snipped off at the said surface (61) of the said muscle (60).

3. A bipolar nerve electrode for permanent implantation into a muscle (600 and adjacent a nerve (580 for stimulation of the nerve, said nerve electrode comprising:
- a first (52) electrode means;
- a cable means (52) coupled to said first electrode, and including a conductor (54) having an exposed distal end which exposed end comprises a second electrode means (54), said first (52) and second (54) electrode means providing opposite polarity electrical energy to the nerve (58);
- an insulating means (53) coupled between said conductor (54) and said first electrode (52); and
- an insulating flap means (57) coupled to said cable means (51) comprising means for coupling said flap means to a surface (61) of the said muscle (60) for shielding adjacent muscle structure from the electrical stimulation provided by said first (52), and second (54) electrodes thereby concentrating the stimulation current field to the nerve,
- said nerve electrode further comprising electrical energy adjusting means for adjusting the amount of electrical energy to be applied to said nerve trunk (58) by adjusting the length of the exposed distal end of said conductor (54), and distance adjusting means for adjusting the distance between the first electrode (52) and second electrode (54) by adjusting the length of insulating means (53) which extends beyond said first electrode (52).

* * * * *